(12) United States Patent
Kahaian et al.

(10) Patent No.: US 8,956,875 B2
(45) Date of Patent: Feb. 17, 2015

(54) WATER HARDNESS MONITORING VIA FLUORESCENCE

(71) Applicant: Ecolab USA Inc., Naperville, IL (US)

(72) Inventors: Arthur J. Kahaian, Chicago, IL (US); Alexandra Knoth, Aurora, IL (US); Hui Li, Naperville, IL (US); Rodney H. Banks, Aurora, IL (US); Joe L. Schwartz, Aurora, IL (US); Sascha J. Welz, Chicago, IL (US)

(73) Assignee: Ecolab USA, Inc., Naperville, IL (US)

( * ) Notice: Subject to any disclaimer, the term of this patent is extended or adjusted under 35 U.S.C. 154(b) by 42 days.

(21) Appl. No.: 13/804,655

(22) Filed: Mar. 14, 2013

(65) Prior Publication Data

US 2014/0273243 A1 Sep. 18, 2014

(51) Int. Cl.
*G01N 33/20* (2006.01)
*G01N 21/64* (2006.01)
(52) U.S. Cl.
CPC .................................. *G01N 21/643* (2013.01)
USPC .................. 436/79; 436/43; 436/50; 436/55; 436/73; 436/172; 422/82.08
(58) Field of Classification Search
USPC .................. 436/43, 50, 55, 73, 79, 164, 172; 422/68.1, 82.05, 82.08; 510/365
See application file for complete search history.

(56) References Cited

U.S. PATENT DOCUMENTS

| | | | |
|---|---|---|---|
| 4,355,072 A | 10/1982 | Mateika et al. | |
| 4,383,043 A * | 5/1983 | Denney et al. | 436/74 |
| 4,457,847 A | 7/1984 | Lorenc et al. | |
| 4,545,920 A | 10/1985 | Lorenc et al. | |
| 4,711,726 A | 12/1987 | Pierce et al. | |
| 4,999,305 A | 3/1991 | Wolcott et al. | |
| 5,041,386 A | 8/1991 | Pierce et al. | |
| 5,094,958 A | 3/1992 | Klainer et al. | |
| 5,173,434 A | 12/1992 | Morris et al. | |
| 5,302,253 A | 4/1994 | Lessard et al. | |
| 5,324,665 A | 6/1994 | Lessard | |
| 5,326,482 A | 7/1994 | Lessard et al. | |
| 5,384,050 A | 1/1995 | Kelley et al. | |
| 5,425,267 A | 6/1995 | Herrmann et al. | |
| 5,462,880 A | 10/1995 | Kane et al. | |
| 5,482,866 A | 1/1996 | Denton et al. | |
| 5,672,515 A | 9/1997 | Furlong | |
| 5,734,098 A | 3/1998 | Kraus et al. | |
| 5,736,405 A | 4/1998 | Alfano et al. | |
| 6,336,058 B1 | 1/2002 | Fowee | |
| 6,436,711 B1 | 8/2002 | Davis et al. | |
| 6,566,139 B2 | 5/2003 | Davis et al. | |
| 6,587,753 B2 | 7/2003 | Fowee | |
| 6,790,664 B2 * | 9/2004 | Bailey et al. | 436/55 |
| 6,790,666 B2 * | 9/2004 | Dang et al. | 436/79 |
| 7,220,382 B2 | 5/2007 | Godfrey et al. | |
| 7,448,255 B2 | 11/2008 | Hoots et al. | |
| 7,951,298 B2 | 5/2011 | Hicks et al. | |
| 7,955,853 B2 | 6/2011 | Hicks et al. | |
| 8,068,033 B2 | 11/2011 | Blokker et al. | |
| 2003/0124730 A1 | 7/2003 | Bailey et al. | |
| 2006/0246595 A1 * | 11/2006 | Banks et al. | 436/86 |
| 2007/0178595 A1 | 8/2007 | Raghuraman et al. | |
| 2008/0179179 A1 | 7/2008 | Hicks et al. | |
| 2008/0202553 A1 | 8/2008 | Hicks et al. | |
| 2009/0177143 A1 | 7/2009 | Markle et al. | |
| 2010/0021958 A1 | 1/2010 | Reed et al. | |
| 2010/0108566 A1 | 5/2010 | Scattergood et al. | |
| 2012/0142113 A1 | 6/2012 | Banks et al. | |

FOREIGN PATENT DOCUMENTS

KR 2008-0069209 A 7/2008

OTHER PUBLICATIONS de Armas et al. Talanta, vol. 52, 2000, pp. 77-82.*
Biwersi et al., "Long-Wavelength Chloride-Sensitive Fluorescent Indicators," *Anal. Biochem.*, 219, pp. 139-143, 1994.
Chalk et al., "Determination of Chloride by Flow Injection Spectrophotometry with Membrane Reagent Injection," *Analytica Chimica Acta*, 366, pp. 147-153, 1998.
Condias GmbH, "Condiapure Water Disinfection Bulletin," 2 pp., 2008.
Dubois et al., "NeSSI™ (New Sampling/Sensor Initiative) Gen II Specification," *Center for Process Anal., Chem*, Univ. of Washington, pp. 1-53, Jun. 24, 2004.
Geddes, Chris, "Optical halide sensing using fluorescence quenching: theory, simulations and applications—a review," *Meas. Sci. and Tech.*, 12, pp. R53-R88, 2001.
Haines et al., "Errors in pH measurement with colorimetric indicators in low alkalinity waters," *Hydrobiologia*, 107, pp. 57-61, 1983.
Hoxter, Gunter, "Suggested Isosbestic Wavelength Calibration in Clinical Analyses," *Clin. Chem.*, 25(1), pp. 143-146, 1979.
Hupert et al., "Conductive diamond thin-films in electrochemistry," *Diamond and Related Materials*, 12, pp. 1940-1949, 2003.
Koparal et al., "Electrochemical oxidation of sulfite ions in aqueous solutions," *Int. J. Environment and Pollution*, 21(6), pp. 579-587, 2004.
Lawrence et al., "Electrochemical Determination of Sulfide at Various Carbon Substrates: A Comparative Study," *Anal. Sci.*, 23, pp. 673-676, 2007.

(Continued)

*Primary Examiner* — Maureen Wallenhorst
(74) *Attorney, Agent, or Firm* — Leydig, Voit & Mayer, Ltd.

(57) ABSTRACT

Provided are automated methods for measuring soluble magnesium concentration in water using fluorescence. The methods employ the use of a pH-buffered liquid and a magnesium coordinating fluorescing reagent. In certain embodiments, the methods may further employ measuring total hardness concentration of the water by displacing any soluble calcium with soluble magnesium and then re-measuring the soluble magnesium concentration. Optionally, the soluble calcium concentration can be determined by subtracting the measured soluble magnesium concentration from the measured total hardness concentration.

29 Claims, 3 Drawing Sheets

(56) References Cited

OTHER PUBLICATIONS

Noiré et al., "A ferrous ion optical sensor based on fluorescence quenching," *Sensors and Actuators B*, 29, pp. 386-391, 1995.

Urbano et al., "Optical Sensor for Continuous Determination of Halides," *Anal. Chem.*, 56(3), pp. 427-429, Mar. 1984.

Waterston et al., "Electrochemical oxidation of sulfide ion at a boron-doped diamond anode," *J. of App. Electrochem.*, 37, pp. 367-373, 2007.

Zhelyaskov et al., "Analysis of nanoliter samples of electrolytes using a flow-through microfluorometer," *Kidney Int'l*, 57, pp. 1764-12769, 2000.

KIPO, International Search Report in International Patent Application No. PCT/US2014/016076, 3 pp. (May 8, 2014).

KIPO, Written Opinion in International Patent Application No. PCT/US2014/016076, 10 pp. (May 8, 2014).

\* cited by examiner

WATER HARDNESS MONITORING VIA FLUORESCENCE

FIELD

The disclosure is directed toward the measurement of soluble magnesium concentration at low concentrations in water entering or re-entering an industrial process.

BACKGROUND

Water used for industrial purposes typically comprises various impurities at low concentrations. Some impurities pose little or no hindrance to the industrial water process, while others can cause inefficiencies. The typical industrial water user may lessen or prevent the inefficiencies caused by known impurities by employing one or more water treatment schemes. For example, possible treatment schemes may include those described in U.S. Pat. Nos. 4,457,847; 4,545,920; 4,711,726; 5,736,405; 5,041,386; 5,384,050; 6,566,139; 6,436,711; 6,587,753; 6,336,058; 7,220,382; 7,448,255; 7,951,298; 7,955,853; and 8,068,033; and U.S. Patent Application Publication Nos. 2008/0202553 and 2008/0179179, the disclosures of each are herein incorporated by reference in their entirety.

Two impurities that may be present in water are soluble calcium and soluble magnesium, commonly known as "hardness." Water may be described as "soft," i.e., generally containing little or no soluble calcium or magnesium; or "hard," i.e., generally having higher (and sometimes undesirably high) concentrations of soluble calcium, soluble magnesium, or both. Hard water can cause known problems in industrial water systems, particularly in thermal industrial water systems, and more particularly in heated thermal industrial water systems such as boiler systems. Some of these known problems may be initiated by concentrations of soluble calcium, soluble magnesium, or both that are not especially high.

Hard water can be softened using one or more water softening procedures, which may include purification using physical or chemical treatment. Non-limiting examples of physical treatment include filtration; distillation; membrane purification including reverse osmosis, forward osmosis, membrane filtration (microfiltration, ultrafiltration, etc.), membrane distillation; ion exchange; and electrochemical methods to precipitate scale. Non-limiting examples of chemical treatment include chelation using at least one chelant such as ethylenediamine tetraacetic acid ("EDTA") or a salt thereof, or precipitation using one or more caustic and/or phosphate compound.

Various analytical methods can be employed to measure hardness in water entering, re-entering, or being used in an industrial process (hereinafter "industrial water"). Hardness concentrations can be measured by inductively coupled plasma ("ICP"), ion selective electrode ("ISE"), light absorbance, titration, atomic absorption ("AA"), or other methods known in the art. While all can produce accurate hardness concentration measurements, each has limitations.

SUMMARY

In a first exemplary embodiment, the present disclosure is directed toward an automated method for monitoring soluble magnesium concentration in industrial water where that industrial water contains soluble magnesium. The automated method comprises combining an aliquot of the water and a quantity of (1) a pH-buffered liquid and (2) a magnesium coordinating fluorescing reagent to produce a buffered water sample. The (2) magnesium coordinating fluorescing reagent coordinates with the soluble magnesium present in the buffered water sample and produces a coordinated magnesium compound. The soluble magnesium concentration in the aliquot of water (and, hence, in the industrial water) can be quantified by using fluorescence measurement to measure the fluorescence produced by the coordinated magnesium compound in the buffered water sample. In this process, the (1) pH-buffered liquid comprises a water soluble, non-coordinating base capable of buffering the (1) pH-buffered liquid to a pH from 8 to 12; and the (2) magnesium coordinating fluorescing reagent is selected from the group consisting of a water soluble, aromatic, ortho hydroxyl substituted azo dye; a water soluble, fused-ring heterocycle; and combinations thereof.

In a second exemplary embodiment, the present disclosure is directed toward an automated method for monitoring and optionally controlling total hardness concentration in industrial water where that industrial water contains soluble calcium and soluble magnesium. The automated method comprises combining an aliquot of water with (4) a magnesium-containing reagent. The (4) magnesium-containing reagent displaces the soluble calcium within the aliquot of water with soluble magnesium, thereby creating a modified water sample having an increased soluble magnesium content. The modified water sample is combined with a quantity of (1) pH-buffered liquid and (2) a magnesium coordinating fluorescing reagent to produce a buffered water sample containing soluble magnesium. The (2) magnesium coordinating fluorescing reagent coordinates with the soluble magnesium present in the buffered water sample to produce a coordinated magnesium compound. The increased soluble magnesium content in the buffered water sample is quantified via fluorescence measurement of the coordinated magnesium compound, which allows for the determination of the total hardness concentration of the aliquot, and hence the industrial water. In this process, the (1) pH-buffered liquid comprises a water soluble, non-coordinating base capable of buffering the (1) pH-buffered liquid to a pH from 8 to 12; and the (2) magnesium coordinating fluorescing reagent is selected from the group consisting of a water soluble, aromatic, ortho hydroxyl substituted azo dye; a water soluble, fused-ring heterocycle; and combinations thereof.

In a third exemplary embodiment, the present disclosure is directed toward an automated method for monitoring and optionally controlling total hardness concentration of industrial water containing soluble calcium and soluble magnesium. The automated method comprises two sets of steps, Group A and Group B, and the sets of steps can be repeated as necessary.

As related to Group A, a first aliquot of water and quantities of (1a) a first pH-buffered liquid, (2a) a first magnesium coordinating fluorescing reagent, and (3a) a first inert fluorescing agent are combined to produce a buffered water sample. The (2a) first magnesium coordinating fluorescing reagent coordinates with the soluble magnesium present in the first aliquot of water creating a coordinated magnesium compound within the buffered water sample. The concentration of any uncoordinated (2a) first magnesium coordinating fluorescing reagent in the buffered water sample is determined by light absorbance. The concentration of the (3a) first inert fluorescing agent in the buffered water sample is determined by fluorescence. The soluble magnesium concentration in the first aliquot of water is also determined by fluorescence measurement of the coordinated magnesium compound in the buffered water sample. Optionally, the soluble magnesium concentration determined via fluorescence measurement of the coordinated magnesium compound is corrected to account for one or more of the following: variation in mixing ratio, variation in background effects, and variation in temperature, thereby allowing for the calculation of an adjusted soluble magnesium concentration in the water.

As related to Group B, a second aliquot of water and quantities of (1b) a second pH-buffered liquid, (2b) a second magnesium coordinating fluorescing reagent, (3b) a second inert fluorescing agent, and (4b) a magnesium-containing reagent are combined creating a modified water sample. The (4b) magnesium-containing reagent reacts with soluble calcium in the second aliquot of water thereby displacing the soluble calcium with soluble magnesium and creating an increased soluble magnesium concentration in the modified water sample. The (2b) magnesium coordinating fluorescing reagent coordinates with the soluble magnesium present in the modified water sample creating a coordinated magnesium compound. The concentration of uncoordinated (2b) magnesium coordinating fluorescing reagent in the modified water sample is measured by light absorbance. The concentration of the inert fluorescing agent in the modified water sample is determined by measuring the fluorescence created by the (3b) inert fluorescing agent in the modified water sample. The soluble magnesium concentration in the modified water sample is measured via fluorescence measurement of the coordinated magnesium compound. The measurement of the soluble magnesium concentration of the modified water sample corresponds to measuring the total hardness concentration in the second aliquot of water, and hence the total hardness concentration in the industrial water. Optionally, the soluble magnesium concentration measured via fluorescence of the coordinated magnesium compound may be corrected to account for one or more of the following: variation in mixing ratio, variation in background effects, and variation in temperature, thereby allowing for the calculation of an adjusted total hardness concentration in the water. Optionally, the soluble magnesium concentration of the first aliquot of water may be subtracted from the total hardness concentration of the second aliquot of water so that the soluble calcium concentration in the water may be determined. Optionally, at least one process variable may be controlled by taking action as a result of the measurements. Furthermore, the (1a) first and (1b) second pH buffered liquids may be the same or different compositions having buffered pH from 8 to 12, the (2a) first and (2b) second magnesium coordinating fluorescing reagent may be the same or different compositions, and the (3a) first and (3b) second inert fluorescing agent may be the same or different compositions.

BRIEF DESCRIPTION OF THE DRAWINGS

The advantages of the present disclosure will become more readily apparent to those of ordinary skill in the relevant art after reviewing the following detailed description and accompanying drawings, wherein.

DETAILED DESCRIPTION

While embodiments encompassing the general inventive concepts may take various forms, there is shown in the drawings and will hereinafter be described various embodiments with the understanding that the present disclosure is to be considered merely an exemplification and is not intended to be limited to the specific embodiments.

The disclosure is generally directed to automated methods for measuring soluble magnesium and/or calcium concentrations (i.e., hardness) in water using fluorescence.

As it pertains to this disclosure, "magnesium coordinating fluorescing reagent" means a chemical compound that is capable of reacting with soluble magnesium to produce a coordinated magnesium compound. The coordinated magnesium compound may vary depending upon the particular magnesium coordinating fluorescing reagent utilized but will be capable of producing a fluorescent emission when coordinated with soluble magnesium and excited by light having a certain wavelength or range of wavelengths. Generally, when added to a water sample that contains soluble magnesium, a quantity of the magnesium coordinating fluorescing reagent coordinates (chemically attaches to soluble magnesium, thereby allowing for the measurement of soluble magnesium concentration via fluorescence) and a quantity may remain uncoordinated (e.g., the amount of the magnesium coordinating fluorescing agent that is residual or excess).

As it pertains to this disclosure, "magnesium-containing reagent" means a chemical compound that is at least partially made up of magnesium and that reacts with a known species that may be present in a substance. For example, in certain embodiments of the methods disclosed herein, the magnesium-containing reagent reacts with soluble calcium that is present in an aliquot of water, thereby displacing the soluble calcium with soluble magnesium.

As it pertains to this disclosure, "overdosing" means providing a molar amount of a particular chemical species that is more than stoichiometrically sufficient such that any chemical equilibrium would shift reasonably quickly as a result of the molar excess. For example, a typical overdosing would be at least ten times the stoichiometric molar amount necessary for a particular chemical reaction.

As it pertains to this disclosure, "water treatment variable" means a measured or calculated value that may be encountered when dealing with water treatment. Examples of water treatment variables include but are not limited to the following: temperature, pressure, flow rate, concentration of one or more chemical species, fluorometric measurements, light or energy absorbance measurements or calculations, ionic measurements/electrical potential (e.g., electrode measurements, etc.), dosage rate, settling rates/times, flotation rates/times, heat exchange rate, density, turbidity, clarity, scaling potential, titration values, flash point, dew point, volume, mass, statistical calculations, and so forth.

As it pertains to this disclosure, "quantifying" means measuring and/or calculating an unknown quantity based on at least one measurement of some kind.

As it pertains to this disclosure, "coordinate" or "coordinated" means a chemical connection of some sort that is sufficiently stable to allow the concentration and/or presence of a chemical species or compound to be measured by the known concentration of another chemical species or compound. For example, a fluorescing reagent may coordinate with a water soluble species in a ratio of one mole of water soluble species to one mole of fluorescing reagent, which would allow a fluorometric measurement of the water soluble species based on the known quantity of fluorescing reagent and/or experimental data related to the coordination of the water soluble species and the fluorescing reagent. Alternatively, the fluorescing reagent may coordinate with a water soluble species in a ratio of one mole of water soluble species to two moles of fluorescing reagent, which would allow a fluorometric measurement of the water soluble species based on the known quantity of fluorescing reagent and/or experimental data related to the coordination of the water soluble species and the fluorescing reagent (e.g., a calibration). The fluorescing reagent is present in excess by design and does not fluoresce until coordination with the water soluble species. In other words, the coordination of the known concentration of the fluorescing reagent allows for the quantification of the concentration of the water soluble species.

As it pertains to this disclosure, "automatic," "automatically," and "automated" mean without human intervention or substantially without human intervention. For example, a process carried out automatically (i.e., an "automated process") would measure a variable and take action (e.g., change a pump speed, open or close a valve, increase heating or cooling, etc.) based on a comparison of the measured variable to a standard value (i.e., a setpoint) without a person having to do anything to make the action take place, outside of initially providing all necessary equipment, plumbing, wiring, power, programming, chemical ingredients, and so forth.

As it pertains to this disclosure, "correcting" means making a change to a measured value based upon one or more variables. For example, a measured value may be knowingly affected by another measurable variable. With knowledge of the existence of the effect, one may correct for the known effect, thereby eliminating the effect in the first measured value. When dealing with fluorometry, effects related to temperature, dilution/concentration, and turbidity can introduce error into the raw fluorescence measurement and frequently require correction of the raw fluorescence measurement to reflect the effect.

As it pertains to this disclosure, "as calcium carbonate" means that the particular concentration measurement (soluble magnesium, soluble calcium, or total hardness) is being reported "as calcium carbonate." Such a reporting method is commonly used in the field and makes uniform the measurement of each species or the total hardness, allowing for comparison across species.

As it pertains to this disclosure, "thermal industrial system" means a process that is responsible for transferring thermal energy (i.e., heat) into or out of an industrial process (e.g., a manufacturing process of some kind) "Thermal industrial water system" further indicates that the thermal industrial system primarily uses water in some form to transfer heat. Examples of thermal industrial water systems include but are not limited to boiler systems, cooling systems, hot water systems, and other systems that are designed to control temperature or transfer thermal energy to or from an industrial process. In certain embodiments, the water that is monitored using the methods disclosed herein is water that is fed into a boiler (i.e., boiler feed water).

As it pertains to this disclosure, "on site" refers to an item located or action taking place within the property borders of an industrial facility. If a process step is performed "on site," it is performed within the property borders of the industrial facility. For example, combining two ingredients to be used in a particular process facility would be performed "on site" if the combining occurred within the property borders of the particular process facility.

Numerical labels (e.g., (1), (2), (1a), (2b), etc.) are sometimes used in the specification and claims. These labels are employed to simplify cross-referencing of elements throughout the claims, particularly between various elements of the independent claims and throughout the dependent claims. The labels are not meant to denote any quantity.

In a first exemplary embodiment, the present disclosure is directed toward an automated method for monitoring soluble magnesium concentration in industrial water where that industrial water contains soluble magnesium. The automated method comprises combining an aliquot of the water and a quantity of (1) a pH-buffered liquid and (2) a magnesium coordinating fluorescing reagent to produce a buffered water sample. The (2) magnesium coordinating fluorescing reagent coordinates with the soluble magnesium present in the buffered water sample and produces a coordinated magnesium compound. The soluble magnesium concentration in the aliquot of water (and, hence, in the industrial water) can be quantified by using fluorescence measurement to measure the fluorescence produced by the coordinated magnesium compound in the buffered water sample. In this process, the (1) pH-buffered liquid comprises a water soluble, non-coordinating base capable of buffering the (1) pH-buffered liquid to a pH from 8 to 12; and the (2) magnesium coordinating fluorescing reagent is selected from the group consisting of a water soluble, aromatic, ortho hydroxyl substituted azo dye; a water soluble, fused-ring heterocycle; and combinations thereof.

In a second exemplary embodiment, the present disclosure is directed toward an automated method for monitoring and optionally controlling total hardness concentration in industrial water where that industrial water contains soluble calcium and soluble magnesium. The automated method comprises combining an aliquot of water with (4) a magnesium-containing reagent. The (4) magnesium-containing reagent displaces the soluble calcium within the aliquot of water with soluble magnesium, thereby creating a modified water sample having an increased soluble magnesium content. The modified water sample is combined with a quantity of (1) pH-buffered liquid and (2) a magnesium coordinating fluorescing reagent to produce a buffered water sample containing soluble magnesium. The (2) magnesium coordinating fluorescing reagent coordinates with the soluble magnesium present in the buffered water sample to produce a coordinated magnesium compound. The increased soluble magnesium content in the buffered water sample is quantified via fluorescence measurement of the coordinated magnesium compound, which allows for the determination of the total hardness concentration of the aliquot, and hence the industrial water. In this process, the (1) pH-buffered liquid comprises a water soluble, non-coordinating base capable of buffering the (1) pH-buffered liquid to a pH from 8 to 12; and the (2) magnesium coordinating fluorescing reagent is selected from the group consisting of a water soluble, aromatic, ortho hydroxyl substituted azo dye; a water soluble, fused-ring heterocycle; and combinations thereof.

In a third exemplary embodiment, the present disclosure is directed toward an automated method for monitoring and optionally controlling total hardness concentration of industrial water containing soluble calcium and soluble magnesium. The automated method comprises two sets of steps, Group A and Group B, and the sets of steps can be repeated as necessary.

As related to Group A, a first aliquot of water and quantities of (1a) a first pH-buffered liquid, (2a) a first magnesium coordinating fluorescing reagent, and (3a) a first inert fluorescing agent are combined to produce a buffered water sample. The (2a) first magnesium coordinating fluorescing reagent coordinates with the soluble magnesium present in the first aliquot of water creating a coordinated magnesium compound within the buffered water sample. The concentration of any uncoordinated (2a) first magnesium coordinating fluorescing reagent in the buffered water sample is determined by light absorbance. The concentration of the (3a) first inert fluorescing agent in the buffered water sample is determined by fluorescence. The soluble magnesium concentration in the first aliquot of water is also determined by fluorescence measurement of the coordinated magnesium compound in the buffered water sample. Optionally, the soluble magnesium concentration determined via fluorescence measurement of the coordinated magnesium compound is corrected to account for one or more of the following: variation in mixing ratio, variation in background effects, and variation in temperature, thereby allowing for the calculation of an adjusted soluble magnesium concentration in the water.

As related to Group B, a second aliquot of water and quantities of (1b) a second pH-buffered liquid, (2b) a second magnesium coordinating fluorescing reagent, (3b) a second inert fluorescing agent, and (4b) a magnesium-containing reagent are combined creating a modified water sample. The (4b) magnesium-containing reagent reacts with soluble calcium in the second aliquot of water thereby displacing the soluble calcium with soluble magnesium and creating an increased soluble magnesium concentration in the modified water sample. The (2b) magnesium coordinating fluorescing reagent coordinates with the soluble magnesium present in the modified water sample creating a coordinated magnesium compound. The concentration of uncoordinated (2b) magnesium coordinating fluorescing reagent in the modified water sample is measured by light absorbance. The concentration of the inert fluorescing agent in the modified water sample is determined by measuring the fluorescence created by the (3b) inert fluorescing agent in the modified water sample. The soluble magnesium concentration in the modified water sample is measured via fluorescence measurement of the coordinated magnesium compound. The measurement of the soluble magnesium concentration of the modified water sample corresponds to measuring the total hardness concentration in the second aliquot of water, and hence the total hardness concentration in the industrial water. Optionally, the soluble magnesium concentration measured via fluorescence of the coordinated magnesium compound may be corrected to account for one or more of the following: variation in mixing ratio, variation in background effects, and variation in temperature, thereby allowing for the calculation of an adjusted total hardness concentration in the water. Optionally, the soluble magnesium concentration of the first aliquot of water may be subtracted from the total hardness concentration of the second aliquot of water so that the soluble calcium concentration in the water may be determined. Optionally, at least one process variable may be controlled by taking action as a result of the measurements. Furthermore, the (1a) first and (1b) second pH buffered liquids may be the same or different compositions having buffered pH from 8 to 12, the (2a) first and (2b) second magnesium coordinating fluorescing reagent may be the same or different compositions, and the (3a) first and (3b) second inert fluorescing agent may be the same or different compositions.

The present disclosure is drawn toward automated reagent based methods of monitoring hardness in water entering or re-entering an industrial process. In certain embodiments, the disclosure is directed toward quantifying a soluble magnesium concentration in an aliquot of water via fluorometric techniques. In certain embodiments, the disclosure is further directed toward using soluble magnesium to displace the soluble calcium contained within an aliquot of water, and then quantifying total hardness of the water via fluorometric techniques.

In certain embodiments, the automated methods disclosed herein involve sampling feed or recycle water from an industrial process in real time and quantifying very low concentrations of the hardness ions calcium and magnesium. The technology involves the use of a molecule that binds with high selectivity to magnesium and fluoresces when coordinated, i.e., a magnesium coordinating fluorescing reagent that produces a coordinated magnesium compound when coordinated with magnesium. In certain embodiments, the fluorescence emitted by the coordinated magnesium compound is linear or essentially linear over the range of zero to 1000 ppb magnesium as calcium carbonate.

Because of the precision necessary to carry out measurements at the relatively low concentrations of soluble calcium and magnesium that are generally contained within the industrial water, the dilution of the agents and reagents must also be carried out with high precision. While certain embodiments of the disclosed automated methods employ high precision pumps, high precision weight measurement devices, and/or high precision flow measurement devices, certain embodiments may employ additional fluorometric and/or absorbance measurements. The fluorometric and/or absorbance measurements are themselves high precision measurements as long as highly precise calibration standards are used for equipment calibration. Any of the previously mentioned devices or measurements may be employed individually or in combination with any or all of the other devices and measurements, depending on the level of sophistication that the user wishes to employ. In certain embodiments, an inert fluorescing agent is employed to allow for precise compensation for errors associated with dilution of the pH-buffered liquid and the magnesium coordinating fluorescing reagent in the aliquot of the water.

In certain embodiments, the methods are capable of monitoring soluble magnesium concentration, soluble calcium concentration, or both (i.e., total hardness) in industrial water. Though the disclosed methods can be practiced using an aliquot of water from various sources, the methods are particularly applicable to water entering or re-entering an industrial process because hard water can be particularly harmful to industrial processes. In certain embodiments, the water is a boiler feed water.

In certain embodiments, the industrial water is reasonably pure so as to avoid interference with the fluorescence measurement (interference with the fluorescence measurement is further explained infra in the present disclosure). In certain embodiments, the industrial water has a total hardness concentration of 2000 ppb or less, measured as calcium carbonate, either naturally or by employing one or more water softening procedures. In certain embodiments, the industrial water is known or believed to have total hardness of 2000 ppb or less even though the exact soluble magnesium or soluble calcium concentrations are unknown. In certain embodiments, the industrial water is known or believed to have a total soluble calcium concentration of no more than 1000 ppb (even though the exact soluble calcium concentration is unknown) and is known or believed to have total soluble magnesium concentration of no more than 1000 ppb (even though the exact soluble magnesium concentration is unknown). In certain embodiments, the industrial process is a thermal industrial system as previously defined.

In certain embodiments, the soluble magnesium concentration in the industrial water is quantified via fluorescence. In certain embodiments, a separate measurement of the soluble magnesium concentration is quantified via fluorescence after the addition of a specific magnesium salt, i.e., a magnesium-containing reagent. The magnesium-containing reagent displaces the dissolved calcium in the water with soluble magnesium at a known ratio, typically one mole of soluble magnesium for each mole of soluble calcium. The displacement allows for the determination of the total hardness concentration that represents all the soluble magnesium and soluble calcium in the water by measurement of the coordinated magnesium compound. In certain embodiments, the soluble calcium concentration is then determined by subtracting a first measured magnesium concentration (representing only soluble magnesium) from the measured total hardness concentration.

In certain embodiments, the method is configured to precisely dose a concentrated reagent in line with boiler feed water that may incorporate the use of at least one diaphragm pump. In certain embodiments, the precise dilution is confirmed and/or corrected by absorbance measurements of the magnesium coordinating fluorescing reagent and fluorescence of at least one inert fluorescing agent. If employed, the inert fluorescing agent should be chosen such that (a) the agent does not react with other species (i.e., is inert), and (b) the agent's fluorescence wavelength should not interfere with the wavelengths of the other fluorescing species. In certain embodiments, the inert fluorescing agent is selected from the group consisting of a derivative of rhodamine, a derivative of fluorescein, and combinations thereof. In certain embodiments, the inert fluorescing agent is Rhodamine WT.

In certain embodiments, the fluorescent intensities are converted to units of ppb as calcium carbonate for magnesium, calcium and/or total hardness.

In certain embodiments, the method is an automated method. In other words, the method steps are carried out automatically or nearly automatically, i.e., without or with only minimal human intervention. In certain embodiments, the only human intervention required is the minimal act of replacing depleted ingredients, including but not limited to the following ingredients or any of their precursors or sub-ingredients: the pH-buffered liquid; the magnesium coordinating fluorescing reagent; the water soluble, non-coordinating base; the inert fluorescing agent; or the magnesium-containing reagent. For automated embodiments, the various passive (sensors) and active components (pumps, valves, etc.) necessary for carrying out the methods will be operably connected to the industrial process and/or a water treatment system at hand. For automated embodiments, the various components are also in communication with a processing unit that has been programmed to logically control the various active components according to parameters that may be set by the user or determined in some other fashion. In certain embodiments, the processing unit may be shared with other control systems employed with the industrial process. In certain embodiments, the processing unit comprises a programmable logic controller ("PLC").

For example, an automated monitoring system may be wired and plumbed so as to perform any sampling and measurement without human intervention, outputting a measured value either constantly or at intervals without a user having to initiate such sampling or measurement. For certain measurements, chemical ingredients must first be combined to an aliquot to trigger fluorescence, and the combining can also be performed automatically using automated controls. In certain embodiments, a powered sensor detects a fluorescence or absorbance at a particular wavelength. The sensor sends a first electrical signal to a control system which in turn may send a second electrical signal to a powered and controlled operation (e.g., a pump or a valve) based on the first electrical signal and user input in the form of a control program, at least one setpoint, and optionally fine tuning. The control system is programmed and may be fine tuned to control around a particular setpoint, for example, based on measured hardness. The control program may control several variables, including flow rates, water softening variables, and the chemistry involved with detecting the hardness. Non-limiting actions that may be taken by the control program include opening a valve to release industrial water (e.g., performing a blowdown cycle), changing the rate or amount of hardness-reducing chemical treatment, and/or acting to remediate pretreatment issues such as switching between water softening salt beds or brine tanks.

As previously discussed, the methods disclosed herein make use of a magnesium coordinating fluorescing reagent. In certain embodiments, the magnesium coordinating fluorescing reagent is selected from the group consisting of a water soluble, aromatic, ortho hydroxyl substituted azo dye; a water soluble, fused-ring heterocycle; and combinations thereof. In certain embodiments, the magnesium coordinating fluorescing reagent is present in the pH-buffered liquid at the time that the pH-buffered liquid is combined with the aliquot of the water. In certain embodiments, the magnesium coordinating fluorescing reagent takes the form of a dry powder and is combined with the pH-buffered liquid on site (or just prior to combining with the aliquot of water). In certain embodiments, the magnesium coordinating fluorescing reagent is combined with the pH-buffered liquid, and the combination is employed while practicing one or more of the disclosed methods within about 28 days of making the combination. In dry form, the magnesium coordinating fluorescing reagent has a lengthy shelf life as compared to the combined substance. Therefore, waiting to combine the dry form until deployment into the process allows the user to take advantage of the lengthy shelf life. In certain embodiments, the magnesium coordinating fluorescing reagent is present in the pH-buffered liquid at a concentration from 1 to 1000 ppm as magnesium coordinating fluorescing reagent.

In certain embodiments, where the magnesium coordinating fluorescing reagent comprises at least one water soluble, aromatic, ortho hydroxyl substituted azo dye, it is selected from the group consisting of Plasmocorinth B, Eriochrome Black T, Calmagite, 8-hydroxyquinolone-5-sulfonic acid, and combinations thereof. In certain embodiments, the magnesium coordinating fluorescing reagent is 8-hydroxyquinolone-5-sulfonic acid ("HQS").

As discussed above, in certain embodiments of the methods disclosed herein, an aliquot of water is combined with a quantity of a pH-buffered liquid and a magnesium coordinating fluorescing reagent to produce a buffered water sample.

As discussed above, the pH-buffered liquid comprises a water soluble, non-coordinating base capable of buffering the pH-buffered liquid, and consequently the aliquot of the water when combined with the pH-buffered liquid, to a pH ranging from 8 to 12. The water soluble non-coordinating base may generally take any form as long as the pH is maintained from 8 to 12, the base is soluble in water, and the base does not coordinate (i.e., does not react) with the metal species in the aliquot, particularly the soluble calcium or soluble magnesium. In certain embodiments, the water soluble, non-coordinating base is capable of buffering the pH-buffered liquid, and consequently the aliquot of the water when combined with the pH-buffered liquid, to a pH ranging from 9 to 11. In certain embodiments, the water soluble, non-coordinating base is a sterically-hindered organic base. In certain embodiments, the water soluble, non-coordinating base is 1,2 diazabicyclo[2.2.2]octane ("DABCO").

The amount or quantity of the pH-buffered liquid that is combined with the aliquot of water can be determined in any one or any combination of several different techniques. In certain embodiments, the amount or quantity of the pH-buffered liquid to be combined with the aliquot of water is determined via mechanical methods (e.g., weight/mass measurements and/or calculations, flow measurements and/or calculations, volume measurements and/or calculations, etc., which may be determined using, e.g., one or more metering pumps, scales, load cells, rotameters, etc.), fluorometry, light absorbance, pressure compensation, flow compensation, and combinations thereof.

In the case of the pH-buffered liquid, it should be understood that the particular amount of the pH-buffered liquid that is combined with the aliquot of water can vary depending upon the size of the aliquot of water and the water concentration within the pH-buffered liquid. In certain embodiments the variation of the particular amount of the pH-buffered liquid is determined by employing an inert fluorescing agent in a known quantity with a known quantity of the pH-buffered liquid, itself having known quantities of ingredients, thereby allowing for fluorescence measurement of the amount of the pH-buffered liquid.

In certain embodiments, the concentration of the pH-buffered liquid in the aliquot is determined using only mechanical methods. Such measurements and/or calculations typically take into account variations in density of the liquids. While usually effective, the aforementioned measurements and calculations ultimately rely on the accuracy and precision of devices such as pumps (e.g., pump speed), weight measurement devices, flow meters, etc., which should be taken into account when sourcing equipment used to carry out the present disclosure.

As previously mentioned, in certain embodiments, the concentration of the pH-buffered liquid in the aliquot is determined via fluorometry. An inert fluorescing agent may be present in the pH-buffered liquid or added to the aliquot at a known inert fluorescing agent-to-pH-buffered liquid ratio, thereby allowing for a fluorometric measurement of the concentration of the inert fluorescing agent in the aliquot. The fluorometric measurement of the inert fluorescing agent in the aliquot allows for the calculation of the concentration of the pH-buffered liquid in the aliquot. The fluorometric measurement of the inert fluorescing agent may be incorporated in combination with one or more mechanical method to confirm the concentration of the pH-buffered liquid in the aliquot that was mechanically measured and/or calculated.

As previously mentioned, the total hardness concentration of a water sample is determined by combining the concentrations of soluble calcium and soluble magnesium present in the water. One technique for measuring the total hardness concentration involves the displacement of either the soluble calcium or the soluble magnesium in favor of the other species and then measuring the total concentration of the favored species.

In certain embodiments, any soluble calcium in an aliquot of the water is displaced with soluble magnesium. In certain embodiments, the soluble calcium is displaced with soluble magnesium by overdosing the aliquot of water with a magnesium-containing reagent, thereby creating a modified water sample. By overdosing, it is meant generally that the displacement employs a molar amount of magnesium-containing reagent that is more than sufficient to displace all of the soluble calcium contained (actual or expected) within the aliquot of water. Depending on factors that may include the particular magnesium-containing reactant and dosage chosen, the displacing of the soluble calcium with soluble magnesium can be time-consuming. Too little dosage will not quickly drive the reaction to completion, but too great a dosage can be wasteful.

As discussed above, in certain embodiments of the methods disclosed herein, the industrial water is known or believed to have a soluble calcium concentration of no more than 2000 ppb or in other embodiments no more than 1000 ppb, the amount of magnesium-containing reagent required to overdose to the extents discussed above can be determined using these maximums. In other embodiments of the methods disclosed herein, the industrial water may be known to have a soluble calcium concentration of not more than a certain amount based upon previous measurements of the soluble calcium concentration in the industrial process, based upon known operating parameters of the industrial process or based upon both.

In certain embodiments, the molar amount of magnesium-containing reagent that is overdosed is 10-10,000 times, alternatively 50-1000 times or 75-500 times, on a molar equivalents basis, the amount required to displace all of the soluble calcium contained within the aliquot of water, whether actual or expected soluble calcium.

In certain embodiments, the magnesium-containing reagent comprises a magnesium-containing multidentate chelant. In certain embodiments, the magnesium-containing multidentate chelant comprises disodium magnesium 1,2-diaminecyclohexyl-N,N,N',N' tetraacetate. In certain embodiments, the magnesium-containing reagent is present in the pH-buffered liquid prior to the pH-buffered liquid being combined with the aliquot of the water. In other embodiments, the magnesium-containing reagent is dosed separate from the pH-buffered liquid.

In certain embodiments of the methods disclosed herein, any or all of the magnesium coordinating fluorescing reagent, the inert fluorescing reagent, and the magnesium-containing reagent can be delivered to the aliquot of the water via the pH-buffered liquid, depending on the concentration measurement carried out by the user (magnesium, total hardness, or magnesium/calcium). For example, if one practicing the disclosure was only interested in measuring the concentration of the soluble magnesium present in a particular water supply, the person may only wish to mix an aliquot of the water with the pH-buffered liquid and the magnesium coordinating fluorescing reagent. Such a practice may depend on several factors, which may include the sophistication of the available equipment, the desired accuracy and/or precision of the measurement, and/or budgetary considerations.

While each of the magnesium coordinating fluorescing reagent, the inert fluorescing reagent, and the magnesium-containing reagent can be delivered to the aliquot of the water via the pH-buffered liquid, it should be understood that the magnesium-containing reagent is introduced into the aliquot only for the measurement of total hardness concentration. Introduction of the magnesium-containing reagent into the aliquot will likely result in the displacement of at least some of the soluble calcium present in the aliquot, should any soluble calcium be present.

In certain embodiments, at least two fluorescence measurements are necessary to determine the concentrations of the two individual species, soluble magnesium and soluble calcium. In certain embodiments, the soluble magnesium concentration in the water is known, but the soluble calcium concentration in the water is unknown, and the soluble calcium concentration is determined by comparing the total hardness concentration to the known magnesium concentration. The soluble magnesium concentration may be known due to practicing the present disclosure or for some other reason.

In certain embodiments, the displacing and the mixing are performed simultaneously, and the magnesium-containing reagent is present in the pH-buffered liquid prior to the pH-buffered liquid being combined with the aliquot of the water.

In certain embodiments, the automated method is repeated as part of an automated monitoring program. In certain embodiments, the automated monitoring program performs the additional function of being a treatment control program. In certain embodiments, the treatment control program is a water softening program.

In certain embodiments, the measured fluorescence of the coordinated magnesium coordinating fluorescing reagent is corrected for process variables. For example, mixing ratio of the agents/reagents, background fluorescence, and temperature may fluctuate during operation of the thermal industrial system and/or the practice of the disclosed methods. These variables can cause errors in measurement of the coordinated magnesium coordinating fluorescing reagent, which can be corrected by comparing the other measurements to known standards.

In certain embodiments, the soluble calcium concentration is determined by subtracting the soluble magnesium concentration from the total hardness concentration. The calculation allows for the total hardness concentration to be further defined by the concentration of each of the two soluble species individually, calcium and magnesium.

As in other fluorescence-based detection methods, the possibility of signal interference exists, i.e., the possibility that a false high reading may occur, depending on the presence of other species in the water. As previously discussed, the methods described herein should employ reasonably pure industrial water.

More specifically, examples of potentially interfering species in the aliquot itself (and in the industrial water) include soluble iron, copper, and zinc. Soluble iron, copper and/or zinc at 100 ppb concentrations or higher can cause interference with fluorescence detection, and in certain embodiments such concentrations in the aliquot of water (and in the industrial water) should be avoided if possible. Thus, in certain embodiments of the methods disclosed herein, the industrial water (and the aliquot of water) contains no more than 100 ppb iron, copper, and/or zinc.

Furthermore, the presence of soluble cadmium at even a very low concentration will compromise the disclosed methods, as cadmium coordinated with the magnesium coordinating fluorescing reagent has a significantly higher fluorescence intensity than magnesium coordinated with the magnesium coordinating fluorescing reagent. Thus, in certain embodiments of the methods disclosed herein, the industrial water (and the aliquot of water) contain 0 ppm of cadmium.

The presence of a high concentration of soluble aluminum or Lanthanum Group elements could potentially interfere with the fluorescence detection of the disclosed methods. The possibility of interference at the lower detection limit of the disclosed methods is possible in the presence of chelants such as EDTA, as these have large formation constants for their calcium and magnesium complexes. Thus, in certain embodiments of the methods disclosed herein, the industrial water (and the aliquot of water) contain no more than a total of 100 ppb of soluble aluminum or Lanthanum Group elements.

Other possible interferences can be caused by using certain materials of construction in the process plumbing. For example, less expensive plastics such as PVC and CPVC should be avoided. In certain embodiments, plumbing materials used to carry out the method include stainless steels and/or higher grade polymers such as PVDF, polysulfone, or polyetherimides.

In certain embodiments, calibration of pumps, flow meters, scales, etc., can be carried out using known methods. In certain embodiments, the fluorometer is calibrated using at least one liquid having a known concentration of soluble magnesium. At low concentrations (e.g., no more than about 1000 ppb magnesium as calcium carbonate), the fluorescence emission is essentially linear, so one calibration point is generally sufficient to establish the calibration. However, multiple calibration points can be tested to ensure accuracy.

Figure 1:
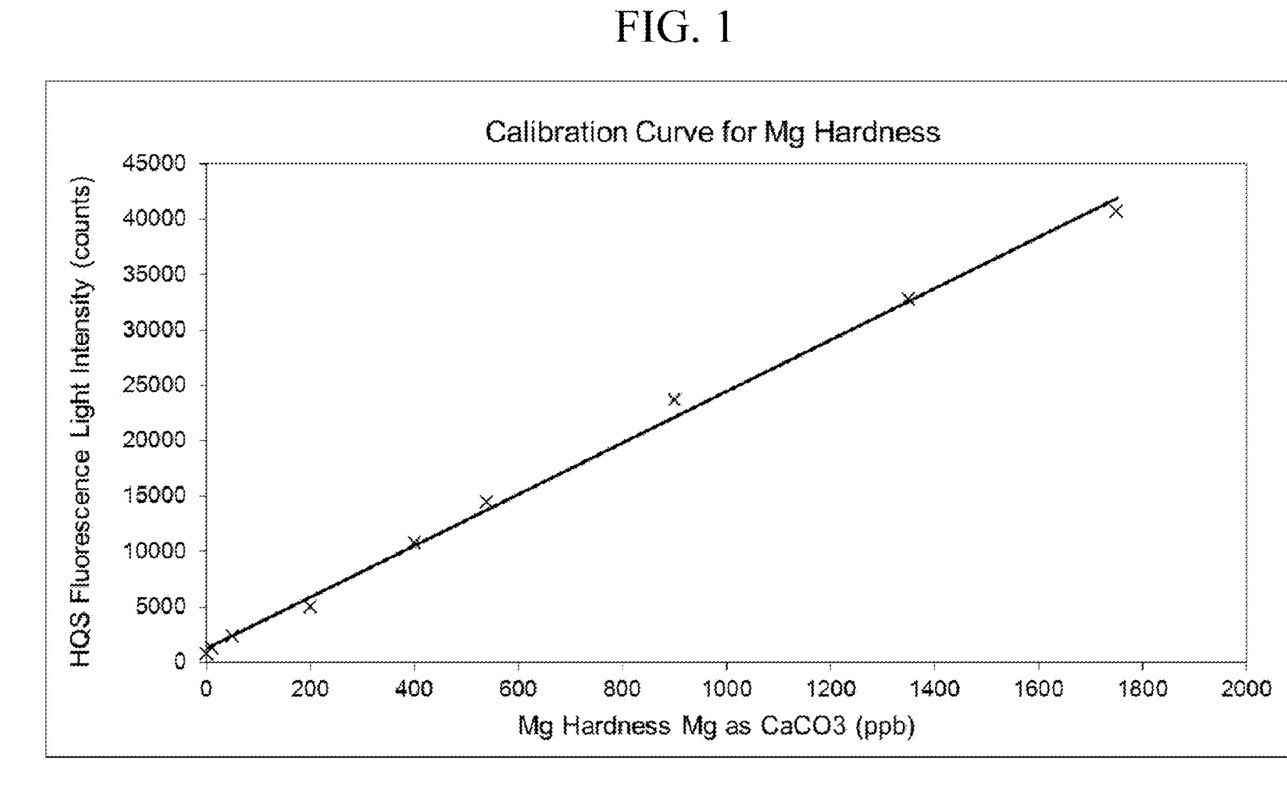
FIG. 1 shows a calibration curve illustrating the linearity of magnesium concentration measured according to one or more methods of the present disclosure, where magnesium concentration is calculated as parts per billion calcium carbonate.

FIG. 1 shows a calibration curve illustrating the linearity of magnesium hardness measured according to one or more methods of the present disclosure, where magnesium concentration is calculated as parts per billion calcium carbonate. To carry out the method, the pH of each sample was buffered to approximately 10.2 and employed HQS as a magnesium coordinating fluorescing reagent at 10 ppm.

Figure 2:
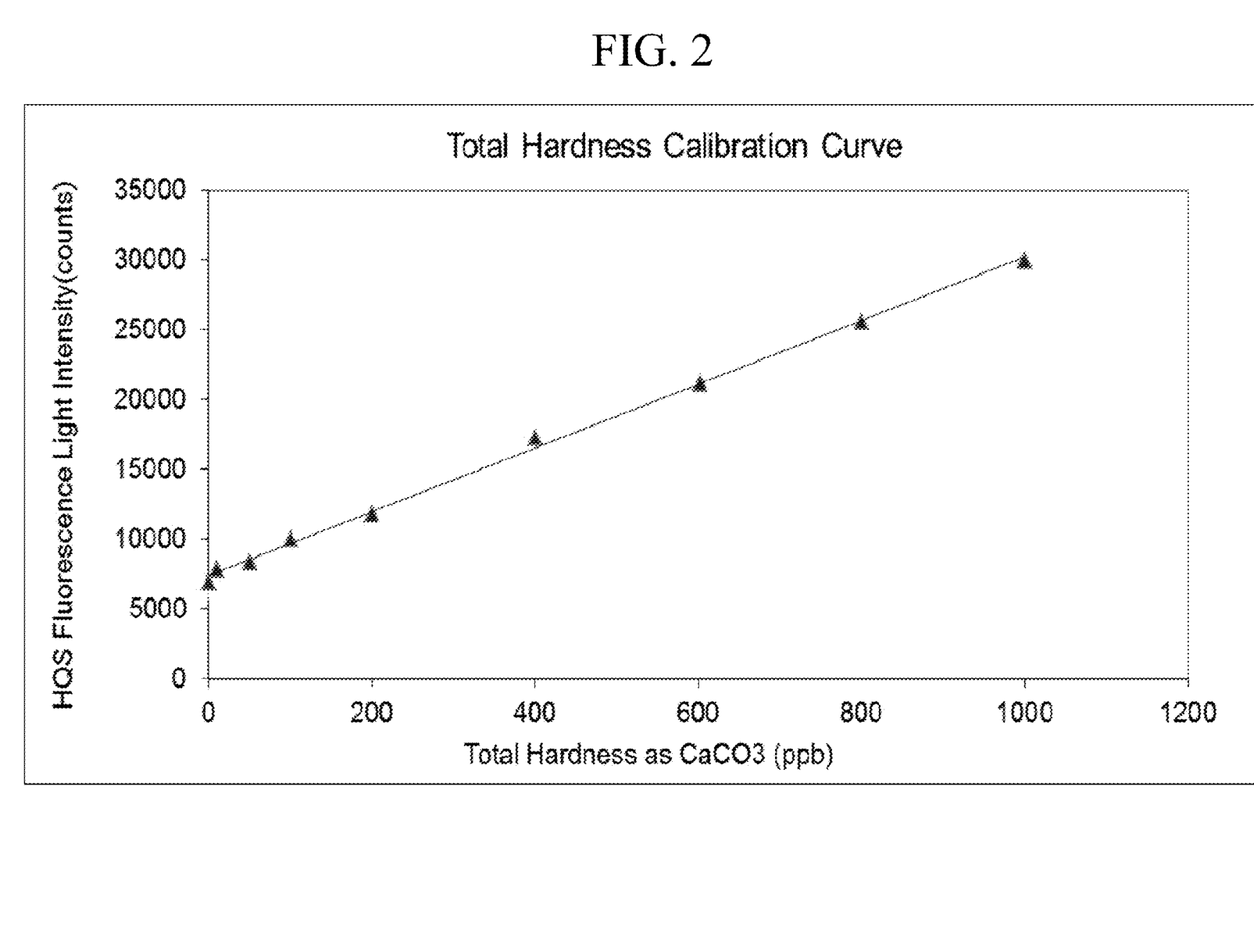
FIG. 2 shows a calibration curve illustrating the linearity of total hardness concentration measured according to one or more methods of the present disclosure, where total hardness concentration is calculated as parts per billion calcium carbonate.

FIG. 2 shows a calibration curve illustrating the linearity of total hardness measured according to one or more methods of the present disclosure, where total hardness concentration is calculated as parts per billion calcium carbonate. To carry out the method, the pH of each sample was buffered to approximately 10.2 and employed HQS as a magnesium coordinating fluorescing reagent at 10 ppm.

Figure 3:
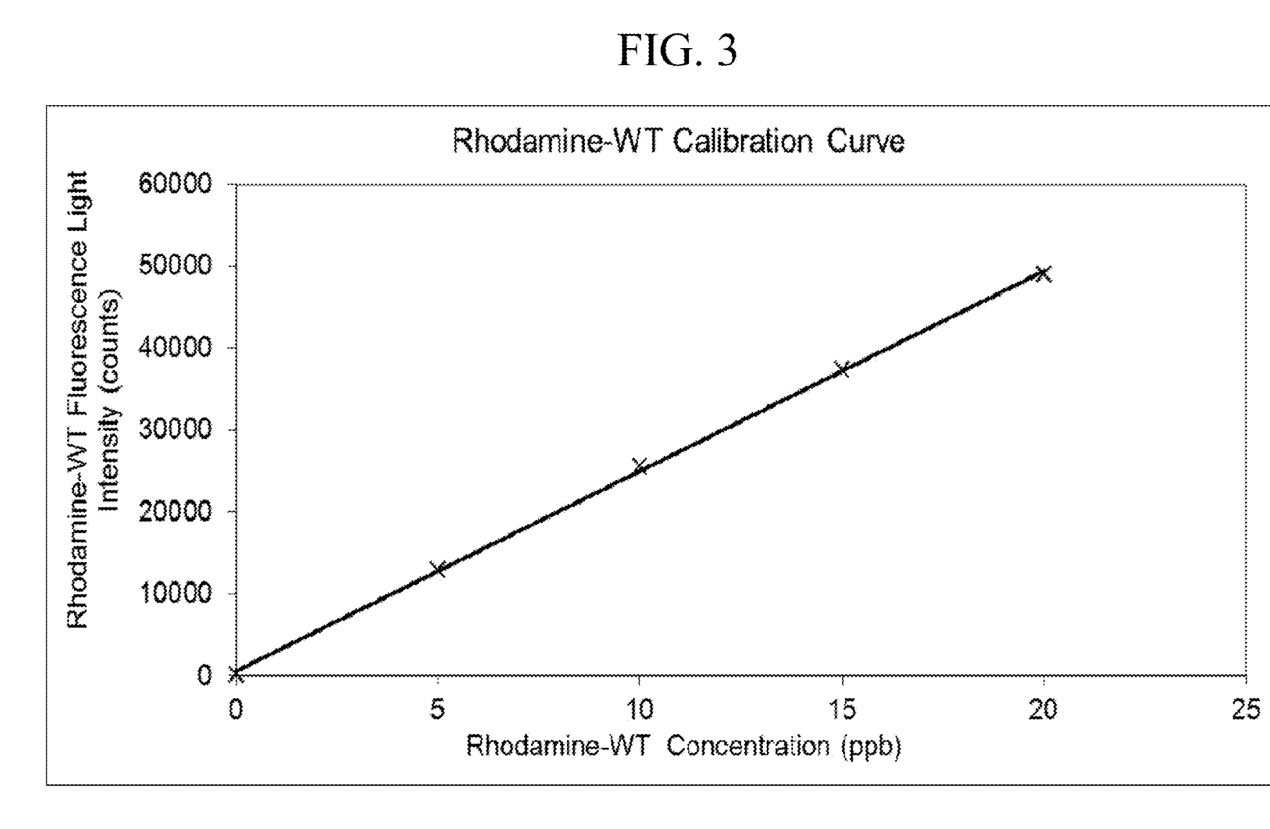
FIG. 3 shows a calibration curve illustrating the linearity of Rhodamine-WT concentration measured according to one or more methods of the present disclosure.

FIG. 3 shows a calibration curve for Rhodamine-WT concentration in water buffered to a pH of approximately 10.2 for each sample.

Any patents referred to herein, are hereby incorporated herein by reference, whether or not specifically done so within the text of this disclosure.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the applicants intend to indicate "only A or B but not both," then the term "only A or B but not both" will be employed. Thus, use of the term "or" herein is the inclusive, and not the exclusive use. See Bryan A. Garner, A Dictionary of Modern Legal Usage 624 (2d ed. 1995). Also, to the extent that the terms "in" or "into" are used in the specification or the claims, it is intended to additionally mean "on" or "onto." Furthermore, to the extent that the term "connect" is used in the specification or the claims, it is intended to mean not only "directly connected to," but also "indirectly connected to" such as connected through another component or components. In the present disclosure, the words "a" or "an" are to be taken to include both the singular and the plural. Conversely, any reference to plural items shall, where appropriate, include the singular.

All ranges and parameters disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The general inventive concepts have been illustrated, at least in part, by describing various exemplary embodiments thereof. While these exemplary embodiments have been described in considerable detail, it is not the Applicant's intent to restrict or in any way limit the scope of the appended claims to such detail. Furthermore, the various inventive concepts may be utilized in combination with one another (e.g., first, second, third, fourth, etc., exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The invention claimed is:

1. An automated method of monitoring soluble magnesium concentration in water containing soluble magnesium, the method comprising:
    combining an aliquot of water and a quantity of (1) a pH-buffered liquid and (2) a magnesium coordinating fluorescing reagent to produce a buffered water sample;
    whereby the (2) magnesium coordinating fluorescing reagent coordinates with the soluble magnesium present in the buffered water sample to produce a coordinated magnesium compound; and
    quantifying the soluble magnesium concentration in the aliquot of water via fluorescence measurement of the coordinated magnesium compound in the buffered water sample;
    wherein the (1) pH-buffered liquid comprises a water soluble, non-coordinating base capable of buffering the (1) pH-buffered liquid to a pH from 8 to 12;
    wherein the (2) magnesium coordinating fluorescing reagent is selected from the group consisting of a water soluble, aromatic, ortho hydroxyl substituted azo dye; a water soluble, fused-ring heterocycle; and combinations thereof; and
    wherein the water soluble, non-coordinating base is 1,2 diazabicyclo[2.2.2]octane.

2. The automated method of claim 1, wherein the (2) magnesium coordinating fluorescing reagent is present in the (1) pH-buffered liquid when combined with the aliquot of water.

3. The automated method of claim 2, wherein the (2) magnesium coordinating fluorescing reagent is a dry powder combined with the (1) pH-buffered liquid on site.

4. The automated method of claim 2, wherein the (2) magnesium coordinating fluorescing reagent is present in the (1) pH-buffered liquid at a concentration from 1 to 50 ppm.

5. The automated method of claim 1, wherein the water has a total hardness concentration greater than zero and not more than 2000 ppb as calcium carbonate.

6. The automated method of claim 1, wherein the (1) pH-buffered liquid is buffered to a pH from 9 to 11.

7. The automated method of claim 1, wherein the (2) magnesium coordinating fluorescing reagent is a water soluble, aromatic, ortho hydroxyl substituted azo dye selected from the group consisting of Plasmocorinth B, Eriochrome Black T, Calmagite, 8-hydroxyquinolone-5-sulfonic acid, and combinations thereof.

8. The automated method of claim 1, wherein the (2) magnesium coordinating fluorescing reagent is 8-hydroxyquinolone-5-sulfonic acid.

9. The automated method of claim 1, wherein (3) an inert fluorescing agent is additionally combined with the aliquot of water at a known (3) inert fluorescing agent-to-(1) pH-buffered liquid ratio, and concentration of the (1) pH-buffered liquid in the aliquot of water is confirmed by fluorescence measurement of the (3) inert fluorescing agent.

10. The automated method of claim 1, wherein the water is boiler feed water.

11. An automated method of monitoring and optionally controlling total hardness concentration in water containing soluble calcium and soluble magnesium, the method comprising:
    combining an aliquot of water with (4) a magnesium-containing reagent whereby the soluble calcium within the aliquot of water is displaced by soluble magnesium, thereby creating a modified water sample having an increased soluble magnesium content;
    combining the modified water sample with a quantity of (1) a pH-buffered liquid and (2) a magnesium coordinating fluorescing reagent to produce a buffered water sample containing soluble magnesium;
    whereby the (2) magnesium coordinating fluorescing reagent coordinates with the soluble magnesium present in the buffered water sample to produce a coordinated magnesium compound;
    quantifying the increased soluble magnesium content in the buffered water sample via fluorescence measurement of the coordinated magnesium compound thereby determining the total hardness concentration of the water;
    wherein the (1) pH-buffered liquid comprises a water soluble, non-coordinating base capable of buffering the (1) pH-buffered liquid and the buffered water sample to a pH from 8 to 12;
    and wherein the (2) magnesium coordinating fluorescing reagent is selected from the group consisting of a water soluble, aromatic, ortho hydroxyl substituted azo dye; a water soluble, fused-ring heterocycle; and combinations thereof.

12. The automated method of claim 11, wherein the (2) magnesium coordinating fluorescing reagent is present in the (1) pH-buffered liquid when the pH buffered liquid is combined with the aliquot of water.

13. The automated method of claim 12, wherein the (2) magnesium coordinating fluorescing reagent is a dry powder combined with the (1) pH-buffered liquid on site.

14. The automated method of claim 12, wherein the displacement of soluble calcium by soluble magnesium occurs simultaneously with the combination of the aliquot of water and the magnesium-containing reagent, and the (4) magnesium-containing reagent is present in the (1) pH-buffered liquid prior to the pH-buffered liquid being combined with the aliquot of water.

15. The automated method of claim 11, wherein the soluble magnesium concentration in the industrial water is known, but the soluble calcium concentration in the water is unknown, and the soluble calcium concentration is determined by subtracting the known magnesium concentration from the total hardness concentration.

16. The automated method of claim 11, wherein the water has a total hardness concentration greater than zero and not more than 2000 ppb as calcium carbonate.

17. The automated method of claim 11, wherein the (1) pH-buffered liquid is buffered to a pH from 9 to 11.

18. The automated method of claim 11, wherein the (2) magnesium coordinating fluorescing reagent is a water soluble, aromatic, ortho hydroxyl substituted azo dye selected from the group consisting of Plasmocorinth B, Eriochrome Black T, Calmagite, 8-hydroxyquinolone-5-sulfonic acid, and combinations thereof.

19. The automated method of claim 11, wherein the (2) magnesium coordinating fluorescing reagent is 8-hydroxyquinolone-5-sulfonic acid.

20. The automated method of claim 11, wherein the (2) magnesium coordinating fluorescing reagent is utilized in an amount sufficient to have a concentration from 1 to 50 ppm in the buffered water sample.

21. The automated method of claim 11, wherein the (1) pH-buffered liquid comprises water and a water soluble non-coordinating base.

22. The automated method of claim 21, wherein the water soluble non-coordinating base is 1,2 diazabicyclo[2.2.2]octane.

23. The automated method of claim 11, wherein the (4) magnesium-containing reagent comprises a magnesium-containing multidentate chelant.

24. The automated method of claim 23, wherein the magnesium-containing multidentate chelant comprises disodium magnesium 1,2-diaminecyclohexyl-N,N,N',N' tetraacetate.

25. The automated method of claim 11, wherein the water is boiler feed water.

26. An automated method of monitoring and optionally controlling total hardness concentration of water containing soluble calcium and soluble magnesium, the method comprising:

A.
   combining a first aliquot of water and quantities of (1a) a first pH-buffered liquid, (2a) a first magnesium coordinating fluorescing reagent, and (3a) a first inert fluorescing agent to produce a buffered water sample;
   whereby the (2a) first magnesium coordinating fluorescing reagent coordinates with the soluble magnesium present in the first aliquot of water to create a coordinated magnesium compound within the buffered water sample;
   determining by light absorbance the concentration of any uncoordinated (2a) first magnesium coordinating fluorescing reagent in the buffered water sample;
   determining by fluorescence the concentration of the (3a) first inert fluorescing agent in the buffered water sample;
   determining the soluble magnesium concentration in the first aliquot of water via fluorescence measurement of the coordinated magnesium compound in the buffered water sample;
   optionally correcting the soluble magnesium concentration determined via fluorescence measurement of the coordinated magnesium compound to account for one or more of the following: variation in mixing ratio, variation in background effects, and variation in temperature, thereby allowing for the calculation of an adjusted soluble magnesium concentration in the water; and
B.
   combining a second aliquot of water and quantities of (1b) a second pH-buffered liquid, (2b) a second magnesium coordinating fluorescing reagent, (3b) a second inert fluorescing agent, and (4b) a magnesium-containing reagent to create a modified water sample,
   whereby the (4b) magnesium-containing reagent reacts with soluble calcium in the second aliquot of water thereby displacing the soluble calcium with soluble magnesium and creating an increased soluble magnesium concentration in the modified water sample and the (2b) magnesium coordinating fluorescing reagent coordinates with the soluble magnesium present in the modified water sample creating a coordinated magnesium compound;
   measuring by light absorbance the concentration of uncoordinated (2b) magnesium coordinating fluorescing reagent in the modified water sample;
   measuring the fluorescence created by the (3b) inert fluorescing agent in the modified water sample in order to determine concentration of the inert fluorescing agent in the modified water sample;
   measuring the soluble magnesium concentration in the modified water sample via fluorescence measurement of the coordinated magnesium compound, the measurement of which corresponds to measuring the total hardness concentration in the second aliquot of water and the total hardness concentration in the water;
   optionally correcting the soluble magnesium concentration measured via fluorescence of the coordinated magnesium compound to account for one or more of the following: variation in mixing ratio, variation in background effects, and variation in temperature, thereby allowing for the calculation of an adjusted total hardness concentration in the water; and
   optionally subtracting the soluble magnesium concentration of the first aliquot of water from the total hardness concentration of the second aliquot of water to arrive at the soluble calcium concentration in the water;
   optionally taking action to control at least one process variable as a result of the measurements; and
   optionally repeating A and B;
   wherein the (1a) first and (1b) second pH buffered liquids are the same or different compositions having buffered pH from 8 to 12, the (2a) first and (2b) second magnesium coordinating fluorescing reagent are the same or different compositions, and the (3a) first and (3b) second inert fluorescing agent are the same or different compositions.

27. The automated method of claim 26, wherein the (4b) magnesium-containing reagent is present in the (1b) pH-buffered liquid at a concentration such that, when added to the second aliquot of water, the (4b) magnesium-containing reagent has a molar concentration from 10 to 10,000 times greater than the soluble calcium concentration.

28. The automated method of claim 26, wherein the quantities of the (2a) magnesium coordinating fluorescing reagent, and the (3a) inert fluorescing agent are present in the (1a) pH-buffered liquid prior to the combining.

29. The automated method of claim 26, wherein the quantities of the (2b) magnesium coordinating fluorescing reagent, the (3b) inert fluorescing agent, and the (4b) magnesium-containing reagent are present in the (1b) pH-buffered liquid prior to the combining.

* * * * *